United States Patent
Yamakawa

(10) Patent No.: US 10,849,930 B2
(45) Date of Patent: Dec. 1, 2020

(54) COMPOSITION FOR PROMOTING INCREASE IN SUBCUTANEOUS TISSUE AND SUBCUTANEOUS ADIPOSE TISSUE

(71) Applicant: Kensuke Yamakawa, Kuwana (JP)

(72) Inventor: Kensuke Yamakawa, Kuwana (JP)

( * ) Notice: Subject to any disclaimer, the term of this patent is extended or adjusted under 35 U.S.C. 154(b) by 0 days.

(21) Appl. No.: 14/370,906

(22) PCT Filed: Feb. 21, 2013

(86) PCT No.: PCT/JP2013/054324
§ 371 (c)(1),
(2) Date: Jul. 7, 2014

(87) PCT Pub. No.: WO2013/125632
PCT Pub. Date: Aug. 29, 2013

(65) Prior Publication Data
US 2015/0004245 A1    Jan. 1, 2015

(30) Foreign Application Priority Data

Feb. 24, 2012 (JP) .................................. 2012-038537

(51) Int. Cl.
| | | |
|---|---|---|
| A61K 35/16 | (2015.01) | |
| A61K 38/18 | (2006.01) | |
| A61L 27/22 | (2006.01) | |
| A61L 27/54 | (2006.01) | |
| A61L 27/36 | (2006.01) | |
| A61K 9/00 | (2006.01) | |
| A61K 9/107 | (2006.01) | |

(52) U.S. Cl.
CPC .......... *A61K 35/16* (2013.01); *A61K 38/1825* (2013.01); *A61L 27/227* (2013.01); *A61L 27/3616* (2013.01); *A61L 27/54* (2013.01); *A61K 9/0041* (2013.01); *A61K 9/107* (2013.01); *A61L 2300/414* (2013.01); *A61L 2430/34* (2013.01)

(58) Field of Classification Search
CPC ............................ A61K 35/16; A61K 38/1825
See application file for complete search history.

(56) References Cited

U.S. PATENT DOCUMENTS

| | | | | |
|---|---|---|---|---|
| 7,316,822 B2 * | 1/2008 | Binette | ............... | A61L 27/3604 424/549 |
| 8,496,702 B2 * | 7/2013 | Rigotti | ...................... | A61F 2/12 623/8 |
| 8,715,653 B2 * | 5/2014 | Turley | ........................ | 424/130.1 |
| 2002/0025340 A1 * | 2/2002 | Dyer | .................... | A61K 9/0019 424/486 |
| 2005/0113937 A1 * | 5/2005 | Binette | ............... | A61L 27/3604 623/23.73 |
| 2009/0157194 A1 * | 6/2009 | Shikinami | .......... | A61B 17/8625 623/23.72 |
| 2009/0317376 A1 * | 12/2009 | Zukowska | ............. | A61K 38/22 424/130.1 |
| 2010/0093622 A1 * | 4/2010 | Lidgren | ................. | A61K 38/30 514/17.4 |
| 2010/0249924 A1 * | 9/2010 | Powell | .................... | A61L 27/18 623/8 |
| 2011/0009960 A1 * | 1/2011 | Altman | ................. | A61F 2/0059 623/8 |
| 2012/0101479 A1 * | 4/2012 | Paspaliaris | ............. | A61K 35/12 604/522 |

(Continued)

FOREIGN PATENT DOCUMENTS

| | | |
|---|---|---|
| JP | 11-199499 A | 7/1999 |
| JP | 2000-302667 A | 10/2000 |

(Continued)

OTHER PUBLICATIONS

Panettiere et al. The Serial Free Fat Transfer in Irradiated Prosthetic Breast Reconstructions; Aesth Plast Surg (2009) 33: 695-700.*
Wikipedia; Adipose Tissue; Online, URL<https://en.wikipedia.org/wiki/Adipose_tissue> 4 pages, accessed Mar. 3, 2016.*
Wikipedia; b-FGF, Online, URL<https://en.wikipedia.org/wiki/Basic_fibroblast_growth_factor> 2 pages, accessed Mar. 3, 2016.*
Joint Guidelines from the Association of Breast Surgery, the British Association of Plastic, Reconstructive and Aesthetic Surgeons, and the British Association of Aesthetic Plastic Surgeons (2012) Lipomodelling Guidelines for Breast Surgery, 28 pages printed from http://www.nvpc.nl/uploads/stand/NVPC120625DOC-MO-richtlijn_bapras_lipofilling108.p.*

(Continued)

*Primary Examiner* — Amy L Clark
(74) *Attorney, Agent, or Firm* — Crowell & Moring LLP

(57) ABSTRACT

In particular, a composition for breast augmentation that includes a composition promoting an increase in subcutaneous tissue, wherein the promoting composition aims at accumulating and increasing adipose tissue under the skin of a breast by generating and increasing the adipose tissue around a mammary gland and enables recovery of autologous tissue and recovery of appearance by a safe and natural process, and a method for breast augmentation are provided. A composition promoting an increase in subcutaneous tissue that contains autologous plasma and a basic fibroblast growth factor (b-FGF), in particular, a composition for breast augmentation is provided. A composition for breast augmentation that includes the above-described composition promoting an increase in subcutaneous tissue that further contains fat is provided. Specifically, a composition for breast augmentation that includes the above-described composition promoting an increase in subcutaneous tissue, wherein the fat is in the form of a lipid emulsion and the lipid emulsion is an oil-in-water lipid emulsion produced by emulsifying fat and oil in the presence of an emulsifier, and a method for breast augmentation by using the composition are provided. An injection unit of the composition for breast augmentation is also provided.

3 Claims, 4 Drawing Sheets

(56) References Cited

U.S. PATENT DOCUMENTS

| | | | | |
|---|---|---|---|---|
| 2012/0269777 A1* | 10/2012 | Van Epps | ............... | A61K 8/49 424/93.7 |
| 2014/0093482 A1* | 4/2014 | Paspaliaris | ............. | A61K 35/12 424/93.7 |
| 2015/0231641 A1* | 8/2015 | Tremolada | .......... | B02C 19/0056 424/93.7 |

FOREIGN PATENT DOCUMENTS

| | | | |
|---|---|---|---|
| JP | 2007-130118 A | 5/2007 | |
| JP | 2008-44890 A | 2/2008 | |
| JP | 2009-235004 A | 10/2009 | |
| JP | 2011-12030 A | 1/2011 | |

OTHER PUBLICATIONS

Nataloni, R. Adipose Stem Cell Developments Oversease Open New Doors for Cosmetic Surgery; Cosmetic Surgery Times, Aug. 1, 2010, Online, URL<http://cosmeticsurgerytimes.modernmedicine.com/cosmetic-surgery-times/news/modernmedicine/modern-medicine-feature-articles/adipose-stem-cell-develo?page=full> 3 pages.*
Regence Medical Policy Manual, Autologous Fat Grafting to the Breast and Adipose-Derived Stem Cells; Nov. 2011, Online, URL<http://blue.regence.com/trgmedpol/surgery/sur182.pdf> 10 pages.*
Sadati et al. The American Journal of Cosmetic Surgery vol. 23, No. 4. 7 pages. (Year: 2006).*
"Fat Transfer". Definition of term. Internet Archive Date: Feb. 16, 2014 [Retrieved from the Internet on: Sep. 18, 2017]. Retrieved from: <URL:https://web.archive.org/web/20140216065303/https://www.smartbeautyguide.com/procedures/injectables/fat-transfer/>. (Year: 2014).*
Chieregato et al. Cytotherapy. vol. 13, Issue 8. Abstract only. (Year: 2011).*
Man et al. Plastic and Reconstructive Surgery: Jan. 2001—vol. 107—Issue 1; p. 229-236 (Year: 2001).*
Alexander, R.W. "Chapter 54: Fat Transfer with Platelet-Rich Plasma for Breast Augmentation" from "Breast Augmentation". Melvin A. Shiffman, Ed. pp. 451-469. (Year: 2009).*
Takeshi Kawazoe et al., "Anti-Aging Treatment Using White Blood Cell-Containing Platelet-Rich Plasma (W-PRP), From Bench To Bedside", The 18th Research Council Meeting of Japan Society of Plastic and Reconstructive Surgery, 2009, (four (4) pages).
Yoshimi Iio et al., "A Clinical and Histological Study On Basic Fibroblast Growth Factor (bFGF)—Containing Platelet Rich Plasma (PRP) Injection Therapy", Journal of Japan Society of Aesthetic Plastic Surgery, 2009, vol. 31, No. 4 (six (6) pages).
Asahi Shinbun, News Paper Article dated Dec. 23, 2008, (two (2) pages).
Yoshiteru Kitami, "Studies on the Lipid Metabolism in the Liver of Rats with Intravenously Injected Fat Emulsion After Partial Hepatectomy", The Japanese Society of gastroenterological Surgery, vol. 30, No. 10, 1987, pp. 2327-2335.
English Translation of Japanese Priority Document for JP 2012-038537, Feb. 24, 2012, pp. 1-33.
Corresponding International Search Report dated May 7, 2013 with English translation (six (6) pages).
PPP Chunyu Ryoho (Plasma Gel) no. Kaigai Shisatsu Joho, Jikoketsu Kesshoban Kessho Filler Seisei Sochi ZeroTherm ni Tsuite, http://www.iryoki.co.jp/news100408.html Apr. 8, 2010 (three (3) pages).
PPP Chunyu Ryoho Guide, http://www.ppp-therapy.com/> 2010, (four (4) pages).
S. Molica et al., Clinicoprognositc implications of increased serum levels of vascular endothelial growth factor and basic fibroblastic growth factor in early B-cell chronic lymphocytic leukaemia, British Journal of Cancer (2002) 86, pp. 31-35.
Http://www/webmd.com/drugs/2/drug-11017/fat-emulsion-intravenous/details , Fat Emulsion Intravenous, Jun. 28, 2016, 3 pages.
https://en.wikipedia.org/wiki/Regenerative_medicine, Regenerative medicine, Jun. 5, 2016, 7 pages.
https://en.wikipedia.org/wiki/Guided_bone_and_tissue_regeneration, Guided bone and tissue regeneration, May 31, 2016, 3 pages.

* cited by examiner

COMPOSITION FOR PROMOTING INCREASE IN SUBCUTANEOUS TISSUE AND SUBCUTANEOUS ADIPOSE TISSUE

TECHNICAL FIELD

The present invention relates to a composition for promoting an increase in subcutaneous tissue that aims at accumulating and increasing subcutaneous tissue or adipose tissue under the skin of a breast and the like by generating and increasing the subcutaneous tissue or the adipose tissue, for example, around a mammary gland.

BACKGROUND ART

It is known that a woman's breast is mainly composed of a mammary gland and adipose tissue and the volume of a breast varies greatly between individuals and also varies readily with increase or decrease in the body weight and the like. It is known that the volume (size) of a breast varies depending on the volume of adipose tissue in a healthy woman.

It has been demonstrated that fat metabolism in adipocytes constituting adipose tissue is different in different body parts. Among others, a breast features a higher level of fat differentiation action as well as a lower level of fat synthesis action compared with a lower leg part and the like. Therefore, in order to maintain an ample breast, it is desirable to promote fat synthesis in the adipocytes thereof and promote increase and accumulation of the adipose tissue thereof and additionally, to prevent the heavy breast from drooping by increasing the subcutaneous tissue thereof.

However, currently, a composition for breast augmentation that is a satisfactory composition for subcutaneous tissue or a satisfactory composition for subcutaneous adipose tissue and solves these problems has not been found yet.

On the other hand, there is a high demand among women to keep an ample breast for the purpose of achieving a beautiful appearance and various breast enlargement operations for this purpose have been performed for a long time.

The first augmentation mammoplasty on a healthy breast for a cosmetic purpose was performed in the United States in the 1950s by using a method of injecting directly paraffin or silicon gel under the skin of a breast. However, this method had a problem that many complications and sequelae such as necrosis of tissue occurred due to the injected paraffin or silicon gel.

Subsequently, a breast implant in which a silicon shell (bag) was filled with silicon gel was developed and furthermore a bag filled with physiological saline instead of silicon was invented. Thus, augmentation mammoplasty by which such a bag was inserted into a chest for a cosmetic purpose had become widely performed.

However, problems surfaced, such as deformation caused by breakage of the bag inserted into the chest or a health hazard occurring in the case of leakage. Therefore, in the United States, the Food and Drug Administration (FDA) placed a moratorium on the use of the silicon gel bag. After that, the physiological saline bag came to be widely used in place of the silicon gel bag.

Furthermore, in the 1995s, a hydrogel bag that included a macromolecular polymer in addition to physiological saline was invented; however, both France and England questioned the safety thereof in the case of long-term use and forbade the use thereof. In 2000, the FDA permitted the use of the physiological saline bag within the United States. Later, a material such as cohesive silicon that had a high viscosity and had fewer dangers in the case of leakage was developed. In 2006, the use of the silicon gel bag was then also permitted.

In Japan, the Ministry of Health, Labour and Welfare has not granted pharmaceutical approval to any breast implants including other breast implants and has not guaranteed the safety thereof.

On the other hand, fat grafting (fat injection) surgery for a breast has started to be performed since the early 1980s as an alternative to the breast implant. However, there are also many negative opinions since fat grafting surgery has an insufficient bust enlargement effect and causes trouble such as interference with the diagnosis of breast cancer in the case of calcification. In recent years, the fat grafting technique has become more advanced and there are fewer risks such as necrosis or calcification of the injected fat. However, this does not mean that all the risks by the fat grafting technique were eliminated completely.

Furthermore, other various proposals regarding breast augmentation have been made frequently and a hyaluronic acid injection method has been in the spotlight as a recently developed breast augmentation method.

This injection of hyaluronic acid into a breast intends to achieve breast augmentation by the injected hyaluronic acid and is also referred to as "petit" breast augmentation since it is easy to perform. However, the effect thereof is temporary and another injection is required for breast augmentation when the hyaluronic acid was absorbed in the body.

However, the injection of hyaluronic acid into a breast disturbs the diagnosis at a medical examination for breast cancer, as the injected hyaluronic acid is often diagnosed as many deep-black cysts. This is a phenomenon called conversion into subcutaneous tissue caused by repeated injections of hyaluronic acid. This conversion of hyaluronic acid into subcutaneous tissue has become a problem with the hyaluronic acid injection method. The hyaluronic acid that was not absorbed into the body and remained after an injection into the subcutaneous tissue is recognized as a foreign substance and not an insignificant number of patients receive extraction of a mammary gland and adjacent tissue of the mammary gland including the injected hyaluronic acid. This problem is expected to become more serious and become a social problem in future.

Furthermore, in addition to those described above, a breast-enlarging agent that includes collagen as an active ingredient (Patent Literature 1), an implant material for breast augmentation treatment that includes at least one kind of cell selected from the group consisting of osteoblasts and chondrocytes and a gel material or a gel precursor material that can gel inside a living body (Patent Literature 2), or the like have been proposed. However, the collagen to be injected itself is a biosynthesized product or derives from a heterologous animal (cattle, swine) and is more likely to cause a biological allergic reaction by hyaluronic acid. Thus, although collagen has a track record of being used for e.g., wrinkle removal, there is a problem that injection of collagen into a breast for breast augmentation cannot be considered to be totally safe.

Furthermore, a breast enlargement-promoting agent that contains a plant-derived ingredient (Patent Literature 3), a breast-enlarging agent that includes extracts obtained by extraction from shellfish as an active ingredient, since many ingredients of such extracts promote breast augmentation (Patent Literature 4), and the like have been proposed. However, currently, a breast-enlarging agent for maintaining an ample breast that promotes fat synthesis in adipocytes and promotes increase and accumulation of adipose tissue has not appeared yet.

Recently, a method for ameliorating a skin problem by promoting an increase in cell tissue, the method including the steps of: combining autologous leucocyte-containing plate rich plasma (PRP) and a growth factor (GF); and injecting the mixture has been proposed (Patent Literature 5). This amelioration of a skin problem aims at suppressing skin dehydration and reduction of skin elasticity mainly resulting from aging, such as a wrinkle or slackness of the skin, and is believed to be applicable to, for example, augmentation mammoplasty. However, plasma separated as PRP is about one tenth to one twentieth of the collected blood volume and up to 400 to 800 mL of blood is required for obtaining 40 mL of PRP. Therefore, available PRP is from at most a few milliliters to at best 40 mL, which is not practical for breast augmentation in which from several tens of milliliters to several hundred milliliters of PRP is required. Thus, it is not examined at all whether this breast augmentation method by using PRP is effective for breast augmentation.

Under the above-described present circumstances, the present inventor focused on plasma among autologous blood components, wherein the plasma is a liquid component making up half of the blood components. The present inventor confirmed that it was possible to aim at accumulating and increasing subcutaneous tissue under the skin of a breast by combining the plasma and a basic fibroblast growth factor (b-FGF) among other growth factors and injecting the combination into the subcutaneous tissue of the breast, in which way, protein as well as a lipid, glucose, and a hormone included in the plasma, particularly the lipid, combined with the effect of the b-FGF. Furthermore, the present inventor also confirmed that it was possible to aim at accumulating and increasing adipose tissue under the skin of a breast very effectively and obtain breast augmentation effect by supplementing an artificial lipid (fat), when the lipid in the plasma was insufficient. In this way, the present invention was accomplished.

PRIOR ART DOCUMENTS

Patent Documents

Patent Literature 1: Japanese Patent Application Laid-Open No. 2008-044890
Patent Literature 2: Japanese Patent Application Laid-Open No. 2007-130118
Patent Literature 3: Japanese Patent Application Laid-Open No. 2000-302667
Patent Literature 4: Japanese Patent Application Laid-Open No. 2011-012030
Patent Literature 5: Japanese Patent Application Laid-Open No. 2009-235004

DISCLOSURE OF INVENTION

Problem to be Solved by the Invention

Therefore, it is an object of the present invention to provide a composition for breast augmentation that is a composition for promoting an increase in subcutaneous tissue and/or subcutaneous adipose tissue, wherein the promoting composition enables recovery of autologous tissue and recovery of appearance by a safe and natural process, and a method for breast augmentation. The inventive composition and the inventive method avoid rupture that is feared to happen with a breast implant that has been used in conventional augmentation mammoplasty, such as cohesive silicon or a silicon gel bag, and the possibility of carcinogenesis, and also avoid induration resulting from conversion of hyaluronic acid into subcutaneous tissue occurring after an injection of hyaluronic acid. The inventive composition and the inventive method aim at accumulating and increasing subcutaneous tissue and adipose tissue under the skin of a breast by generating and increasing the adipose tissue around a mammary gland. It is also an object of the present invention to aim at promoting an increase in subcutaneous tissue and/or adipose tissue in a body part other than a breast.

Means for Solving the Problem

To solve these problems, in a basic aspect, the present invention provides a composition for promoting an increase in subcutaneous tissue that contains autologous plasma and a basic fibroblast growth factor (b-FGF).

Specifically, the present invention provides the above-described composition for promoting an increase in subcutaneous tissue, wherein the subcutaneous tissue is subcutaneous cell tissue and/or subcutaneous adipose tissue.

More specifically, the present invention provides a composition for promoting an increase in subcutaneous tissue that further contains fat, wherein the fat is in the form of a lipid emulsion and the lipid emulsion is an oil-in-water lipid emulsion produced by emulsifying fat and oil in the presence of an emulsifier.

Most specifically, the present invention provides a composition for breast augmentation that includes the above-described composition for promoting an increase in subcutaneous tissue used for breast augmentation.

Furthermore, in another aspect, the present invention provides a method for promoting an increase in subcutaneous tissue including injecting subcutaneously the above-described composition for promoting an increase in subcutaneous tissue. Specifically, the present invention provides a method for breast augmentation including injecting subcutaneously a composition for breast augmentation that includes such compositions for promoting an increase in subcutaneous tissue.

Furthermore, in another aspect, the present invention provides an injection unit of a composition promoting an increase in subcutaneous tissue that includes the above-described composition for promoting an increase in subcutaneous tissue. Specifically, the present invention provides an injection unit for breast augmentation that includes a composition for breast augmentation containing autologous plasma and a basic fibroblast growth factor (b-FGF).

More specifically, the present invention provides an injection unit for breast augmentation that includes a composition for breast augmentation further containing fat, wherein the fat is in the form of a lipid emulsion, and specifically, the lipid emulsion is an oil-in-water lipid emulsion produced by emulsifying fat and oil in the presence of an emulsifier.

Effects of the Invention

The present invention avoids rupture of a bag that is feared to happen with conventional augmentation mammoplasty by insertion of a breast implant, for example, augmentation mammoplasty using cohesive silicon or a silicon gel bag and the possibility of carcinogenesis caused thereby, and also avoids induration resulting from conversion of hyaluronic acid into subcutaneous tissue occurring after an injection of hyaluronic acid. Thus, the present invention provides a composition for promoting an increase for subcutaneous tissue by a safe and natural process, and in particular, provides a composition for breast augmentation that is a composition for subcutaneous adipose tissue that produces a significant effect in breast augmentation.

The composition for promoting an increase in subcutaneous tissue provided by the present invention enables recovery of autologous tissue and recovery of appearance by a natural process by promoting formation of subcutaneous tissue topically and also promoting fat synthesis in adipocytes, thereby generating and increasing subcutaneous cell tissue and/or adipose tissue.

The composition for promoting an increase in subcutaneous tissue provided by the present invention aims at accumulating and increasing subcutaneous cell tissue and/or subcutaneous adipose tissue under the skin of a breast, in particular, by generating and increasing breast adipose tissue, and enables recovery of autologous tissue and recovery of appearance by a natural process. The inventive composition for promoting an increase in subcutaneous tissue has a great medical effect in that it provides a composition for breast augmentation and a method for breast augmentation that use safe means.

MODES FOR CARRYING OUT THE INVENTION

Figure 1:
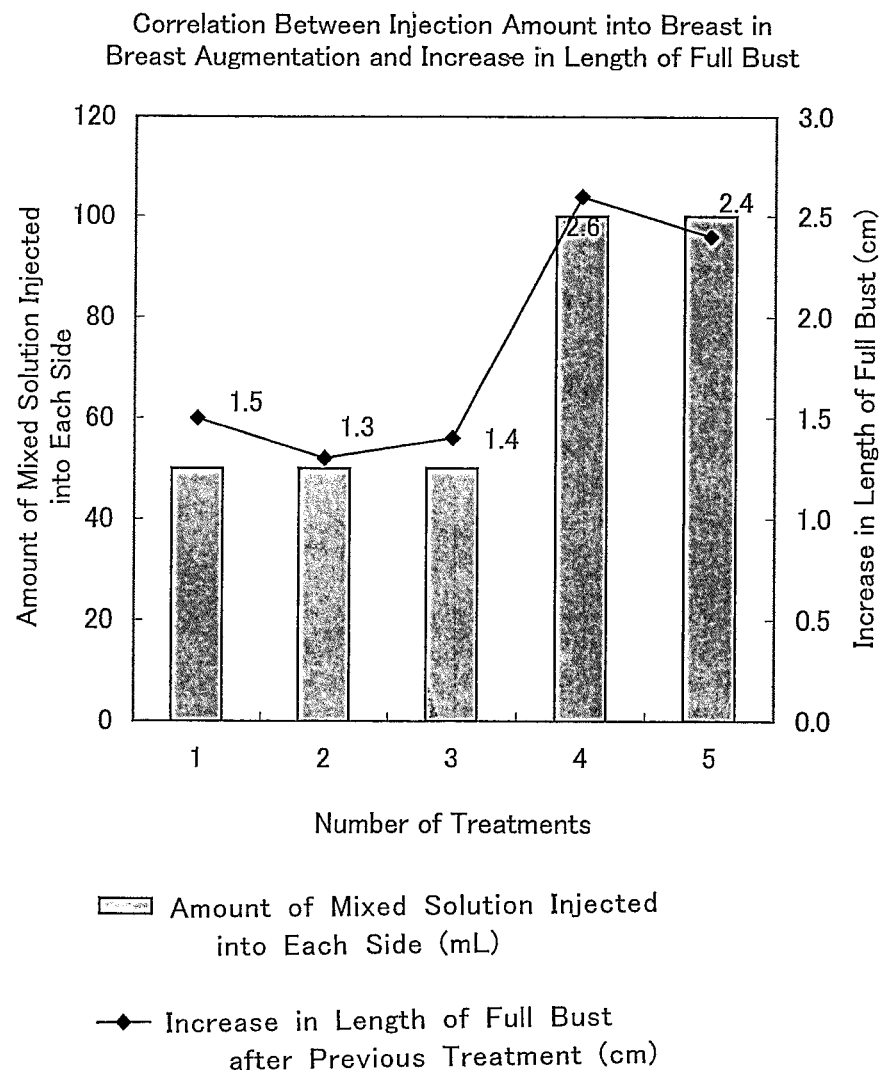
FIG. 1 is a graph showing the results of one example of actual augmentation mammoplasty (Example 2: case 1) by using a composition for breast augmentation that is the composition for promoting an increase in subcutaneous tissue of the present invention.

As described above, a basic aspect of the present invention is a composition for promoting an increase in subcutaneous tissue that contains autologous plasma and a basic fibroblast growth factor (b-FGF).

The subcutaneous tissue that is increased and promoted in the present invention is subcutaneous cell tissue and/or subcutaneous adipose tissue.

Therefore, another aspect of the present invention is a composition for breast augmentation when used in breast augmentation, in that the composition aims at promoting an increase in subcutaneous cell tissue and/or subcutaneous adipose tissue of a breast.

The present invention will be described below by focusing on the composition for breast augmentation used in breast augmentation of a breast; however, the same description applies to cosmetics and aesthetics by promoting an increase in subcutaneous tissue of a body part other than a breast, which is a purpose of the present invention.

Autologous plasma is plasma obtained by collecting one's own blood and centrifuging the blood by a conventional method and is the liquid component that makes up approximately 55% of blood.

This component contains many organic constituents, for example, protein, as well as nonprotein nitrogen, a lipid, glucose, a hormone, and an antibody. Plasma is a blood component that is not only nutritionally important as a protein reserved within the body but also is responsible for many roles such as modulation of the amount of blood or body fluid, a blood coagulation factor, preparation of blood pressure by making blood viscous, transport of a bound substance, or involvement in immunity.

Specifically, autologous plasma in a gel form can be prepared as follows. Blood (autologous blood) is collected from a human on whom breast augmentation by using the composition for breast augmentation of the present invention is to be performed. The blood is centrifuged at a maximum of 4,000 rpm, preferably within 3,000 to 4,000 rpm to separate the plasma. Then, heparin or citric acid, which is an anticoagulant, is added to the plasma.

The composition for breast augmentation provided by the present invention is a composition in which such autologous plasma is combined with a basic fibroblast growth factor (b-FGF).

A basic fibroblast growth factor (b-FGF) is a factor that was discovered as a protein that promotes proliferation of fibroblasts significantly. Later, it was revealed that this basic fibroblast growth factor not only promotes proliferation of fibroblasts in vitro but also has a promoting effect on the proliferation, migration, and differentiation of various cells, such as a vascular endothelial cell, a vascular smooth muscle cell, or an epithelial cell.

The mechanism of action of this factor is as follows: this factor specifically binds to a FGF receptor that exists on a vascular endothelial cell, a fibroblast, and the like, and exerts an angiogenesis effect and a granulation-promoting effect. This factor induces proliferation of a fibroblast, which is a connective fibrous cell that plays an important role in the formation of an organ, at a proliferative phase in the process of wound healing, while the factor promotes apoptosis in the process leading to reconstruction, thereby reducing the number of fibroblasts and making a scar smaller. Therefore, this factor is clinically used as a therapeutic drug for a bed sore and a skin ulcer.

In the present invention, a product that is produced as a recombinant by expression of a genomic gene for a human-derived basic fibroblast growth factor and is clinically used as a recombinant basic fibroblast growth factor can be used. Specifically, a product that has a generic name "Trafermin" and is marketed with a trade name "Fiblast (registered trademark) spray" by Kaken Pharmaceutical Co., Ltd. can be used as it is.

The composition for breast augmentation provided by the present invention is a composition for promoting an increase in subcutaneous tissue that combines the above-described autologous plasma and a basic fibroblast growth factor (b-FGF). It is aimed at generating and increasing adipose tissue around a mammary gland thereby accumulating and increasing adipose tissue under the skin of a breast, by administrating the composition for breast augmentation that includes the above-described composition for promoting an increase in subcutaneous tissue between the mammary gland of a breast and a pectoralis major fascia. It is preferable to administer fat at the same time if necessary in order to generate and increase a greater amount of adipose tissue.

Such fats include fats that have biocompatibility when administered into a living body. Specifically, the following can be illustrated as representative examples: a triglyceride of long-chain fatty acids (LTC) (preferably, the carbon number of the long-chain fatty acid is 11 to 24) as a source of an essential fatty acid, such as a vegetable oil (refined soybean oil, cotton seed oil, safflower oil, corn oil, coconut oil, perilla oil, linseed oil, and the like) or a fish oil (sardine oil, cod liver oil, and the like); and a triglyceride that is characteristically easy to absorb, easy to burn, and difficult to accumulate, for example, a triglyceride of medium-chain fatty acids (MCT) that usually includes fatty acids with a carbon number of 8 to 10, such as Panasate (trade name, manufactured by NOF Corporation) or ODO (trade name, manufactured by the Nissin Oillio Group, Ltd.).

Preferably, the fat is administered in the form of a lipid emulsion, specifically, an oil-in-water lipid emulsion produced by emulsifying fat and oil such as the above-described refined soybean oil in the presence of an emulsifier.

For example, it is favorable that the fat and oil be included in a generally prepared oil-in-water emulsion so that the concentration of the fat and oil falls within approximately 0.5 to 30% (v/v), preferably 0.5 to 20% (v/v), and more preferably 0.5 to 10% (v/v). In this context, it goes without saying that the dose is not limited to the above-described amount and can be increased or reduced where appropriate.

Commonly used emulsifiers, such as a phospholipid (refined egg yolk lecithin, hydrogenated egg yolk lecithin, soybean lecithin, hydrogenated soybean lecithin, and the like) or a synthetic surface active agent (e.g., a commercial product such as Tween 80, HCO-60 (polyoxyethylene hydrogenated castor oil), or Pluronic F68) can be used as an emulsifier for emulsifying and dispersing the above-described fats and oils. One of these may be used alone, or two or more of these may be used in combination.

For example, "Intrapilid (registered trademark) infusion" formulation provided as a lipid emulsion for intravenous injection by Fresenius Kabi Japan K.K. can be favorably used as such a lipid emulsion.

This "Intrapilid (registered trademark)" is an oil-in-water lipid emulsion used as a nutritional supplement, wherein the lipid emulsion is produced by emulsifying refined soybean oil by using refined egg yolk lecithin (an emulsifier), concentrated glycerin (an isotonic agent), and sodium hydroxide (a pH regulator) as additives.

It is recommended to administer the composition for breast augmentation provided by the present invention, in one breast augmentation treatment, at a dose of 50 to 200 mL of the composition per treatment, and then, administer the above-described composition for several, preferably approximately 10 breast augmentation operations while monitoring the breast-enlarging effect after administration thereof. The administration interval is desirably one treatment per approximately one to three months.

It is preferable that the dose of autologous plasma be 25 to 100 mL/treatment, the dose of a basic fibroblast growth factor (b-FGF) be 2.5 to 5 µg of the above-described "Trafermin"/mL/treatment, and fat be administered e.g., at a dose of 0 to 0.2 g of refined soybean oil/mL/treatment, while monitoring the breast-enlarging effect thereof.

In this context, it goes without saying that the dose is a dose from which a general breast-enlarging effect is obtained and that a dose is not limited to the above-described dose and can be increased or reduced where appropriate.

The composition for breast augmentation provided as described above that includes the composition for promoting an increase in subcutaneous tissue of the present invention generates and increases adipose tissue around a mammary gland, thereby generating and increasing adipose tissue under the skin of a breast, when administered between the mammary gland of a breast and a pectoralis major fascia. In this way, the composition for breast augmentation achieves the intended breast augmentation. The composition for breast augmentation also promotes formation of subcutaneous tissue in human skin in a body part other than a chest by acting as a composition for promoting an increase in subcutaneous tissue, and therefore, can be used cosmetically and aesthetically.

Therefore, in yet another aspect, the present invention provides a method for breast augmentation by using a composition for breast augmentation that includes the composition for promoting an increase in subcutaneous tissue of the present invention. Furthermore, the present invention provides an injection unit of the composition for breast augmentation used in the method for breast augmentation, that is, an injection unit of the composition for breast augmentation that includes the composition for promoting an increase in subcutaneous tissue prepared by combining autologous plasma and a basic fibroblast growth factor (b-FGF), and furthermore fat if necessary. The present invention also provides an injection unit that also promotes formation of subcutaneous tissue under a human skin in a body part other than a chest by acting as a composition for promoting an increase in subcutaneous tissue.

The unit doses of the autologous plasma and the basic fibroblast growth factor (b-FGF), and the fat added if necessary in the injection unit of the composition for breast augmentation are set as appropriate within the dose range described above.

EXAMPLES

Hereinbelow, the present invention will be described in more detail by describing a specific method for preparing a composition for promoting an increase in subcutaneous tissue and a composition for breast augmentation that includes the above-described composition, and the practice of augmentation mammoplasty by using the above-described composition for breast augmentation.

However, it goes without saying that the present invention is not limited to those, various modifications may be performed as long as the modifications do not deviate from the claims, and such modifications are also encompassed in the present invention.

Example 1: Preparation of a Composition for Breast Augmentation that Includes a Composition Promoting an Increase in Subcutaneous Tissue <Preparation of Autologous Plasma>

For blood collection, 2.5 mL of heparin sodium (10 units/mL) was added to a syringe having a syringe volume of 50 cc and 50 mL of blood was collected. In total, 220 to 300 mL of blood was collected. The collected blood was centrifuged (a combination of KUBOTA 2420 and KUBOTA RS-240 (a rotor), at 4,000 rpm for 10 minutes) to separate plasma.

25 mL of the separated plasma was collected in a 50 cc syringe, thereby obtaining heparinized plasma.

In order to obtain heated autologous plasma, after the heparinized plasma was obtained, the heparinized plasma was subjected to a heat treatment of the plasma at 100° C. for 10 minutes by using a dry thermo unit (Dry Thermo Unit DTU-1C by TAITEC Corporation) and subsequently, the plasma was cooled rapidly. Consequently, heated autologous plasma in a gel form was obtained.

<Preparation of a Composition for Breast Augmentation that Includes a Composition Promoting an Increase in Subcutaneous Tissue>

A Trafermin (registered trademark) formulation (a recombinant basic fibroblast growth factor: b-FGF by Kaken Pharmaceutical Co., Ltd.) was dissolved in and mixed with an accompanying solution so that the concentration of Trafermin became 2.5 μg/mL. This solution was mixed with the unheated or heated plasma (25 mL) obtained as described above and then, if necessary, 25 mL of Intralipid (registered trademark) infusion 20% (manufactured by Fresenius Kabi Japan K.K.) as a lipid emulsion was added to each syringe. In this way, a composition for breast augmentation that included the composition promoting an increase in subcutaneous tissue of the present invention was prepared in a total amount 50 mL, the composition being composed of a mixed solution of autologous plasma, a basic fibroblast growth factor (b-FGF), and a lipid emulsion.

When no Intralipid was added, 50 mL of heparinized plasma was collected in a 50 cc syringe and Trafermin was added and mixed with the plasma so that the concentration of Trafermin became 2.5 μg/mL.

Further compositions for breast augmentation that included the composition promoting an increase in subcutaneous tissue of the present invention were prepared by using various conditions. For example, the concentration of the added Trafermin (registered trademark) formulation was changed from 2.5 μg/mL to 5.0 μg/mL, or no lipid emulsion (Intralipid (registered trademark) infusion) was added.

Hereinbelow, actual clinical cases in which the composition for breast augmentation that included the composition promoting an increase in subcutaneous tissue of the present invention obtained according to the above-described Example was used are described.

In the following clinical cases, in addition to autologous plasma, "Trafermin" was used as a basic fibroblast growth factor (b-FGF) and "Intralipid" was used as a lipid emulsion.

Example 2: A Specific Example of Administration of a Composition for Breast Augmentation that Includes a Composition Promoting an Increase in Subcutaneous Tissue (Case 1)

The composition for breast augmentation of the present invention was administered to a 45-year-old woman to whom sufficient informed consent was given in advance and who gave consent, and the effect of breast augmentation was evaluated.

The composition for breast augmentation that included the composition promoting an increase in subcutaneous tissue prepared according to the above-described Example 1 was used. A mixed solution of Trafermin, Intralipid (a lipid emulsion), and the heparinized autologous plasma was administered between the mammary gland and the pectoralis major fascia five times.

In the first to the third administrations, 50 mL for each side, that is, 100 mL in total was administered. In the fourth and the fifth administrations, 100 mL for each side, that is, 200 mL in total was administered. The concentration of the lipid emulsion was 50% (v/v) and the concentration of Trafermin was 2.5 μg/mL.

The result is shown in FIG. 1.

As is clear from the result shown in the figure, the length of full bust was increased only by approximately 1.5 cm when the mixed solution of Trafermin, the lipid emulsion (Intralipid), and the heparinized autologous plasma was administered in an amount of 50 mL on each side; while the length of full bust was increased by approximately 2.5 cm when the mixed solution was administered thereafter in an amount of 100 mL on each side.

It was found from this result that the breast-enlarging effect by administration of the composition for breast augmentation that included the composition promoting an increase in subcutaneous tissue of the present invention was varied in relation to the dose of the administered composition for breast augmentation that included the composition promoting an increase in subcutaneous tissue of the present invention.

Example 3: A Specific Example of Administration of a Composition for Breast Augmentation that Includes a Composition Promoting an Increase in Subcutaneous Tissue (Case 2)

The composition for breast augmentation of the present invention was administered to a 36-year-old woman to whom sufficient informed consent was given in advance and who gave consent, and the effect of breast augmentation was evaluated.

First, it was determined which factor was necessary in a mixed solution of Trafermin, a lipid emulsion (Intralipid), and heparinized autologous plasma that constituted the composition for breast augmentation of the present invention.

Initially, the composition for breast augmentation that included the composition promoting an increase in subcutaneous tissue of the present invention, the inventive composition being composed of a mixed solution of Trafermin and heparinized autologous plasma and including no lipid emulsion (Intralipid) was administered three times. Consequently, the length of full bust was increased by approximately 1.1 cm.

Subsequently, at the time of the fourth and the fifth administrations, a composition for breast augmentation that included the composition promoting an increase in subcutaneous tissue further including a lipid emulsion (Intralipid) at a concentration of 50% (v/v) was administered. The concentration of Trafermin was 2.5 μg/mL at the time of the fourth administration of the composition for breast augmentation of the present invention and 5.0 μg/mL at the time of the fifth administration.

Consequently, the increase in the length of full bust after the fourth administration was approximately 2.4 cm, and the increase in the length of full bust after the fifth administration was 4.1 cm.

Figure 2:
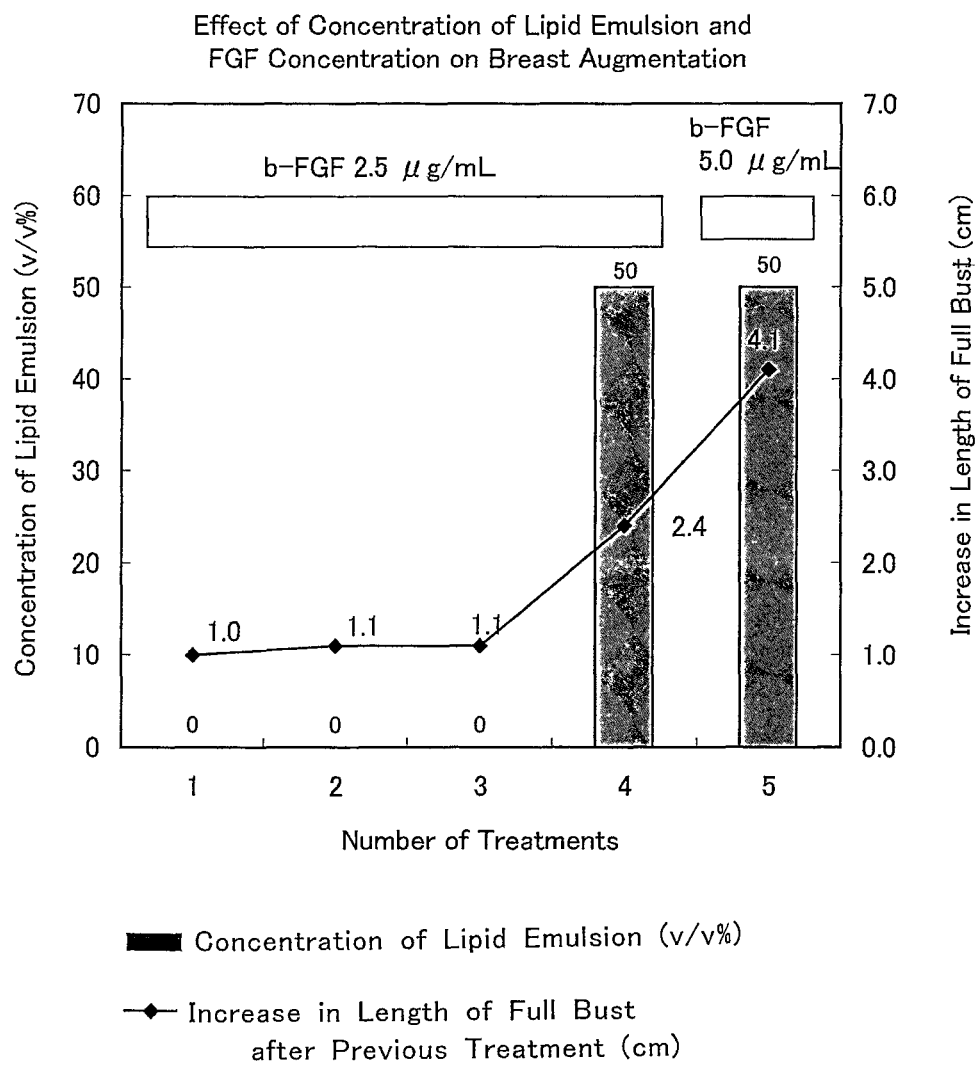
FIG. 2 is a graph showing the results of another example of actual subcutaneous tissue formation and augmentation mammoplasty (Example 3: case 2) by using a composition for breast augmentation that is the composition for promoting an increase in subcutaneous tissue of the present invention.

The result is shown in FIG. 2.

As is also found from the result shown in the figure, although an increase in the breast volume was seen when the composition for breast augmentation that included the composition promoting an increase in subcutaneous tissue of the present invention was administered, the inventive composition being based on a combination of autologous plasma and Trafermin, the increase was small. The effect of increasing breast volume was enhanced by adding a lipid emulsion (Intralipid) to this combination.

Based on this fact, the increase in breast volume (increase in the length of full bust) by the mixed solution of heparinized autologous plasma, Trafermin, and a lipid emulsion (Intralipid), which was the composition for breast augmentation of the present invention, was understood to be attributed partially to a composition promoting an increase in subcutaneous tissue that depended on a lipid emulsion (Intralipid) and partially to a composition promoting an increase in subcutaneous tissue that depended on Trafermin and heparinized autologous plasma.

Moreover, it was found that the increase in the length of full bust attributed to heparinized autologous plasma was stimulated positively and enhanced by an increase in the concentration of Trafermin.

Example 4: A Specific Example of Administration of a Composition for Breast Augmentation that Includes a Composition Promoting an Increase in Subcutaneous Tissue (Case 3)

Objective person is a 40-year-old woman. The woman herself hoped to receive breast augmentation by using heated autologous plasma. For that reason, after sufficient informed consent was given to her in advance and her consent was obtained, a composition for breast augmentation that included the composition promoting an increase in subcutaneous tissue of the present invention was administered to her and the effect of breast augmentation was evaluated.

The composition for breast augmentation prepared according to Example 1 that was composed of a mixed solution of heparinized heated autologous plasma, Trafermin, and a lipid emulsion (Intralipid) was administered in an amount of 50 mL for each side, that is, 100 mL in total, three times. However, the length of full bust did not change.

To remove any doubt whether the subject's plasma had a problem, at the time of the fourth to the sixth administrations, 100 mL of a mixed solution of Trafermin and heparinized unheated autologous plasma without a lipid emulsion was administered. As a result, approximately 1 cm of increase in the length of full bust independent of a lipid emulsion was observed as with the above-described case 2 (Example 3).

Then, at the time of the seventh and the eighth administrations, a composition for breast augmentation that included the composition promoting an increase in subcutaneous tissue of the present invention, the inventive composition being composed of a mixed solution of heparinized unheated autologous plasma, Trafermin, and a lipid emulsion (Intralipid) was administered in an amount of 50 mL for each side, that is, in a total amount of 100 mL. Consequently, 3 cm of increase in the length of full bust was observed.

In this case, the concentration of Trafermin was 2.5 µg/mL and the concentration of the lipid emulsion (Intralipid) was 50% (v/v).

Figure 3:
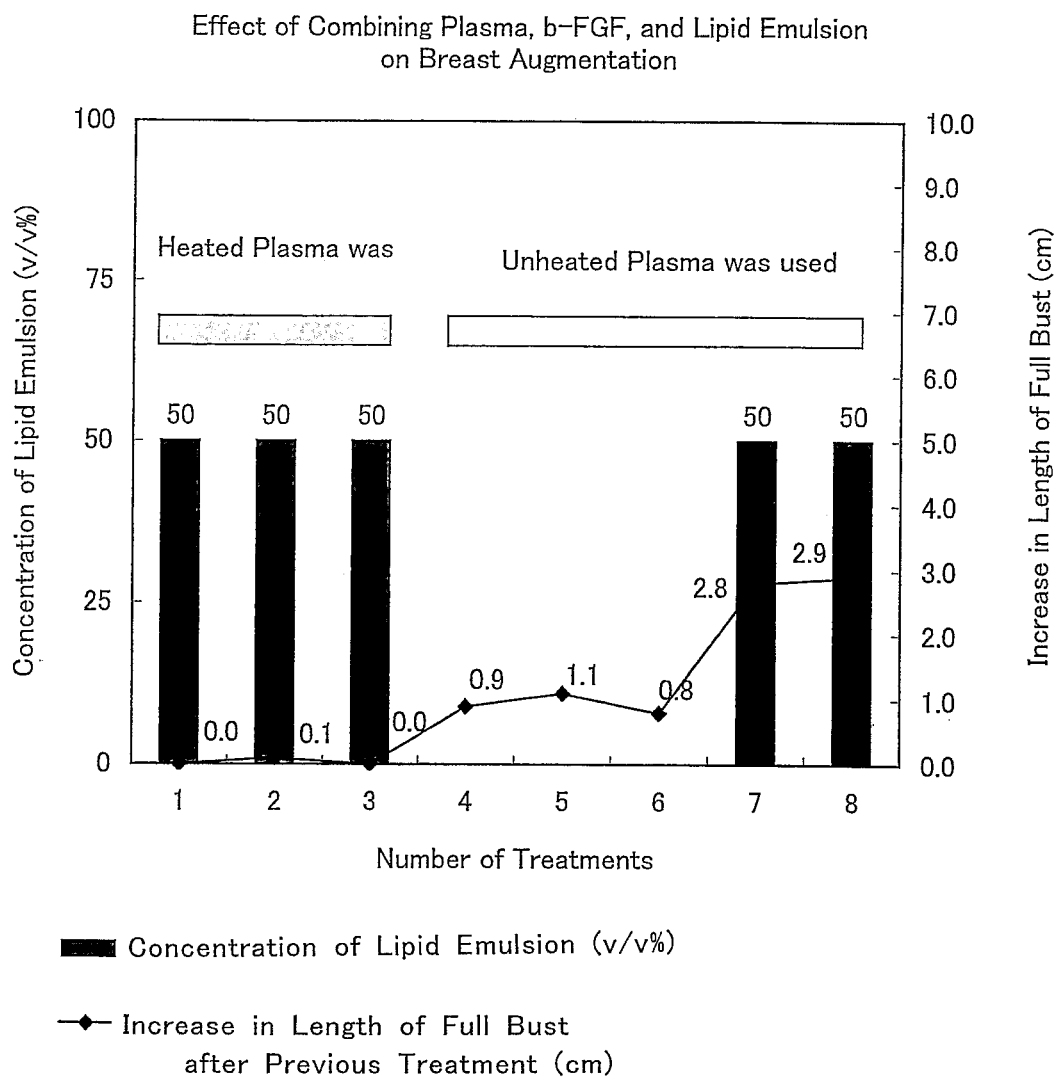
FIG. 3 is a graph showing the results of another example of actual subcutaneous tissue formation and augmentation mammoplasty (Example 4: case 3) by using a composition for breast augmentation that is the composition for promoting an increase in subcutaneous tissue of the present invention.

The result is shown in FIG. 3.

Figure 4:
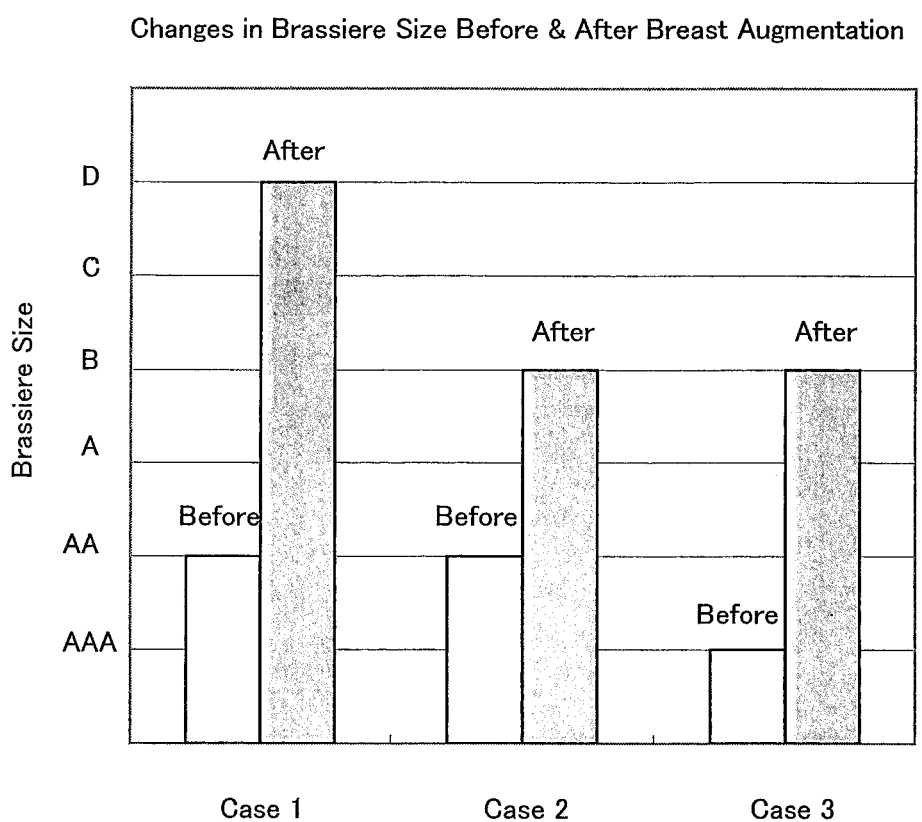
FIG. 4 is a graph showing change of the brassiere size of the subjects in the cases 1 to 3 in which a composition for breast augmentation that is the composition for promoting an increase in subcutaneous tissue of the present invention was used.

The change in the subjects' brassiere size in the above-described Examples 2 to 4 (cases 1 to 3) is shown in FIG. 4.

In every case, the brassiere size was increased by 2 to 4 sizes.

The codes for brassiere size have a meaning that is defined in Table 1 below.

TABLE 1

| Brassiere Size | Difference between Length of Full Bust and Length of Under Bust |
|---|---|
| AAA | Approx. 5.0 cm |
| AA | Approx. 7.5 cm |
| A | Approx. 10.0 cm |
| B | Approx. 12.5 cm |
| C | Approx. 15.0 cm |
| D | Approx. 17.5 cm |

INDUSTRIAL APPLICABILITY

As described above, the present invention avoids problems that had occurred in conventional augmentation mammoplasty by inserting a breast implant or breast augmentation such as by an injection of hyaluronic acid and provides a composition for breast augmentation that produces breast augmentation effect by a safe and natural process.

A composition for breast augmentation that includes the composition promoting an increase in subcutaneous tissue provided by the present invention aims at accumulating and increasing adipose tissue under the skin of a breast by promoting formation of subcutaneous tissue and promoting fat synthesis in adipocytes, thereby generating and increasing the adipose tissue in a breast. The composition for breast augmentation enables recovery of autologous tissue and recovery of appearance by a natural process.

Therefore, the present invention has a great industrial applicability in that it provides a composition for breast augmentation and a method for breast augmentation, wherein the composition and the method are based on promoting increase in subcutaneous tissue and/or subcutaneous adipose tissue by safe means in breast augmentation.

The invention claimed is:

1. A method for promoting an increase in subcutaneous tissue, comprising injecting subcutaneously a dose of 50 to 200 mL of a composition per treatment, the composition comprising autologous plasma, a basic fibroblast growth factor (b-FGF) and fat wherein (a) 25 ml to 100 ml of autologous plasma is administered per treatment, (b) the b-FGF is in an amount of 2.5 to 5 µg per ml per treatment, and (c) the fat is in a lipid emulsion form comprising 0.5 to 30% v/v of fat and oil, and wherein injecting the composition promotes an increase in subcutaneous tissue.

2. A method for breast augmentation, comprising subcutaneously injecting into a breast a dose of 50 to 200 mL of a composition per treatment, the composition comprising autologous plasma, a basic fibroblast growth factor (b-FGF) and fat wherein (a) 25 ml to 100 ml of autologous plasma is administered per treatment, (b) the b-FGF is in an amount of 2.5 to 5 µg per ml per treatment and (c) the fat is in a lipid emulsion form comprising 0.5% to 30% (v/v) of fat and oil, and wherein injecting the composition promotes an increase in subcutaneous adipose tissue.

3. The method of claim 1, wherein the lipid emulsion is an oil-in-water lipid emulsion produced by emulsifying fat and oil in the presence of an emulsifier.

* * * * *